(12) United States Patent
Bedingham et al.

(10) Patent No.: US 11,116,401 B2
(45) Date of Patent: Sep. 14, 2021

(54) SYSTEMS AND METHODS FOR WIRELESS PHYSIOLOGY MONITORING

(71) Applicant: 3M INNOVATIVE PROPERTIES COMPANY, Saint Paul, MN (US)

(72) Inventors: William Bedingham, Woodbury, MN (US); Jeffrey G. Zinn, Roseville, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/348,016

(22) PCT Filed: Nov. 6, 2017

(86) PCT No.: PCT/US2017/060169
§ 371 (c)(1),
(2) Date: May 7, 2019

(87) PCT Pub. No.: WO2018/132162
PCT Pub. Date: Jul. 19, 2018

(65) Prior Publication Data
US 2019/0282095 A1 Sep. 19, 2019

Related U.S. Application Data

(60) Provisional application No. 62/421,063, filed on Nov. 11, 2016.

(51) Int. Cl.
*A61B 5/00* (2006.01)
*A61B 90/98* (2016.01)
(Continued)

(52) U.S. Cl.
CPC ............ *A61B 5/002* (2013.01); *A61B 5/0006* (2013.01); *A61B 5/303* (2021.01); *A61B 5/318* (2021.01);
(Continued)

(58) Field of Classification Search
CPC ....... A61B 5/002; A61B 5/6823; A61B 5/044; A61B 5/04286; A61B 5/7445;
(Continued)

(56) References Cited

U.S. PATENT DOCUMENTS

| 5,307,818 | A | 5/1994 | Segalowitz |
| 5,458,122 | A | 10/1995 | Hethuin |

(Continued)

FOREIGN PATENT DOCUMENTS

| CN | 103230261 | 8/2013 |
| WO | WO 90/09143 | 8/1990 |

(Continued)

OTHER PUBLICATIONS

"LifeSync® 2.1 System", User's Manual, LifeSync Corporation, 2013, pp. 1-69.

(Continued)

*Primary Examiner* — James J Yang
(74) *Attorney, Agent, or Firm* — Sriram Srinivasan; X. Christina Huang; Jonathan V. Sry

(57) ABSTRACT

At least some aspects of the present disclosure direct to systems and methods for monitoring a physiological condition with a plurality of sensors. The system includes a wireless adaptor device and a wireless sensor device. The wireless adaptor device is configured to transmit wireless identification of the wireless adaptor device to the wireless sensor device via a NFC communication. The wireless sensor device is configured establish a wireless communication with the wireless adaptor device using the wireless identification of the wireless adaptor device. The wireless sensor device is further configured to transmit sensor signals to the wireless adaptor device via the established wireless communication.

11 Claims, 13 Drawing Sheets

(51) Int. Cl.
*G16H 40/63* (2018.01)
*G06K 7/10* (2006.01)
*H04B 5/00* (2006.01)
*A61B 5/30* (2021.01)
*A61B 5/318* (2021.01)
*A61B 5/339* (2021.01)

(52) U.S. Cl.
CPC ............ *A61B 5/339* (2021.01); *A61B 5/6823* (2013.01); *A61B 5/7445* (2013.01); *A61B 90/98* (2016.02); *G06K 7/10297* (2013.01); *G16H 40/63* (2018.01); *H04B 5/0031* (2013.01); *A61B 5/0002* (2013.01); *A61B 2562/222* (2013.01); *A61B 2562/227* (2013.01)

(58) Field of Classification Search
CPC ..... A61B 5/0402; A61B 5/0006; A61B 90/98; A61B 5/0002; A61B 2562/227; A61B 2562/222; H04B 5/0031; G06K 7/10297; G16H 40/63
See application file for complete search history.

(56) References Cited

U.S. PATENT DOCUMENTS

| | | |
|---|---|---|
| 5,682,902 A | 11/1997 | Herleikson |
| 9,084,530 B2 * | 7/2015 | Duesterhoft ......... A61B 5/0022 |
| D814,323 S | 4/2018 | Bedingham |
| 2007/0027388 A1 * | 2/2007 | Chou ................... A61B 5/0002 600/393 |
| 2010/0234746 A1 | 9/2010 | Sebelius |
| 2011/0145894 A1 | 6/2011 | Garcia Morchon |
| 2014/0313052 A1 * | 10/2014 | Yarger ..................... A61B 5/72 340/870.02 |
| 2015/0282708 A1 | 10/2015 | Schlottau |
| 2015/0359429 A1 | 12/2015 | Al-Ali |
| 2016/0286287 A1 | 9/2016 | Slack |
| 2018/0200140 A1 * | 7/2018 | Ganske ..................... B32B 5/26 |

FOREIGN PATENT DOCUMENTS

| | | |
|---|---|---|
| WO | WO 97/10747 | 3/1997 |
| WO | WO 97/18639 | 5/1997 |
| WO | WO 99/44494 | 9/1999 |
| WO | WO 00/62664 | 10/2000 |
| WO | WO 00/62665 | 10/2000 |
| WO | WO 2018-089302 | 5/2018 |

OTHER PUBLICATIONS

International Search Report for PCT International Application No. PCT/US2017/060169, dated Jul. 19, 2018, 4 pages.

Supplementary European Search Report for EP Application No. 17 89 1497 dated Jun. 8, 2020, 5 pages.

* cited by examiner

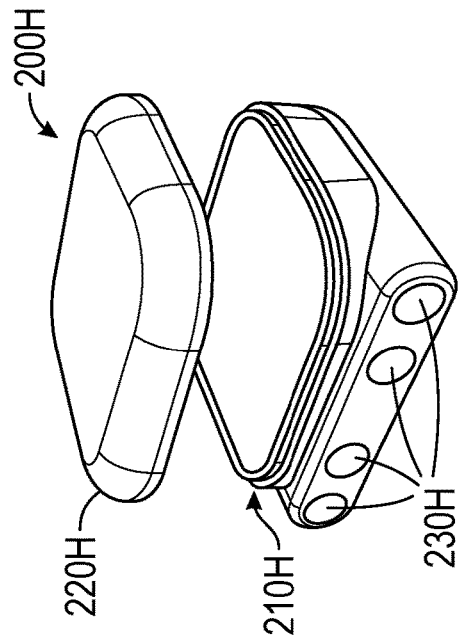
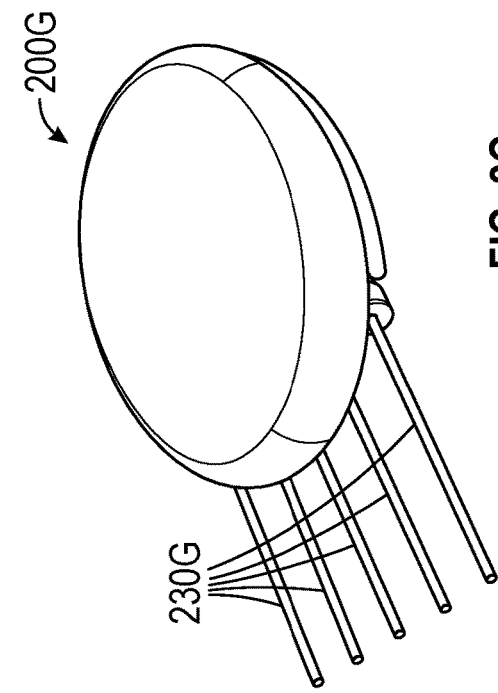
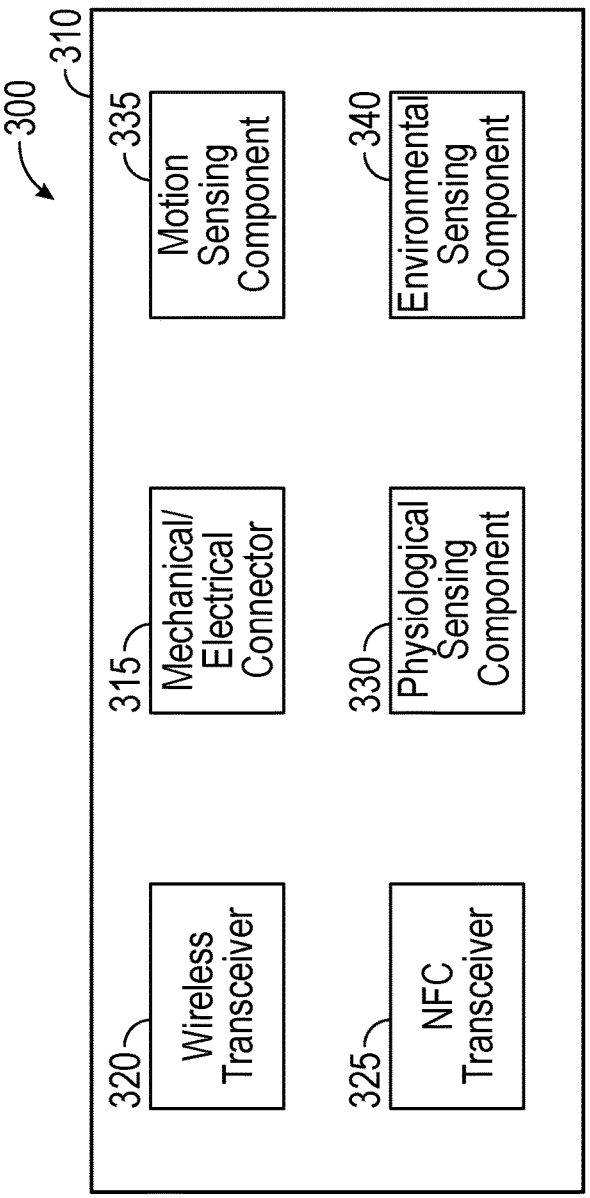
FIG. 2H
FIG. 2G
FIG. 3

SYSTEMS AND METHODS FOR WIRELESS PHYSIOLOGY MONITORING

CROSS REFERENCE TO RELATED APPLICATIONS

This application is a national stage filing under 35 U.S.C. 371 of PCT/US2017/060169, filed Nov. 6, 2017, which claims the benefit of U.S. Provisional Application No. 62/421,063, filed Nov. 11, 2016, the disclosure of which is incorporated by reference in its entirety herein.

TECHNICAL FIELD

The present disclosure is related to wireless physiological sensor systems, components, and methods of using the systems.

SUMMARY

At least some aspects of the present disclosure direct to a wireless physiology monitoring system. The wireless physiology monitoring system includes a plurality of sensors, a wireless sensor device electrically connected to the plurality of sensors and a wireless adaptor device. The wireless sensor device includes a first wireless transceiver. The wireless sensor device is mechanically and electrically connected to one of the plurality of sensors. The wireless sensor device is configured to receive sensing signals from the plurality of sensors and wirelessly transmit a sensor signal indicative to the sensing signals via the first wireless transceiver. The wireless adaptor device includes a second wireless transceiver and configured to wirelessly receive the sensor signal via the second wireless transceiver.

At least some aspects of the present disclosure direct to a method of monitoring a physiological condition with a plurality of sensors. The method includes the steps of: placing a wireless adaptor device proximate to a wireless sensor device, the wireless sensor device electrically connected to the plurality of sensors and having a first wireless transceiver and a first NFC transceiver, the wireless adaptor device having a second wireless transceiver and a second NFC transceiver; transmitting, by the wireless adaptor device, wireless identification of the wireless adaptor device to the wireless sensor device via a NFC communication; establishing, by the wireless sensor device, a wireless communication with the wireless adaptor device using the wireless identification of the wireless adaptor device; collecting, by the wireless sensor device, sensing signals generated by the plurality of sensors; generating, by the wireless sensor device, a sensor signal indicative to the sensing signals; transmitting, by the wireless sensor device, the sensor signal via the established wireless communication; and receiving, by the wireless adaptor device, the sensor signal via the established wireless communication.

At least some aspects of the present disclosure direct to a method of monitoring a physiological condition with a plurality of sensors. The method includes the steps of: placing a wireless adaptor device proximate to a wireless sensor device, the wireless sensor device electrically connected to the plurality of sensors and having a first wireless transceiver and a first NFC transceiver, the wireless adaptor device having a second wireless transceiver and a second NFC transceiver; transmitting, by the wireless sensor device, wireless identification of the wireless sensor device to the wireless adaptor device via a NFC communication; establishing, by the wireless adaptor device, a wireless communication with the wireless sensor device using the wireless identification of the wireless sensor device; collecting, by the wireless sensor device, sensing signals generated by the plurality of sensors; generating, by the wireless sensor device, a sensor signal indicative to the sensing signals; transmitting, by the wireless sensor device, the sensor signal via the established wireless communication; and receiving, by the wireless adaptor device, the sensor signal via the established wireless communication.

BRIEF DESCRIPTION OF DRAWINGS

The accompanying drawings are incorporated in and constitute a part of this specification and, together with the description, explain the advantages and principles of the invention. In the drawings.

FIGS. 2A-2H illustrate several example embodiments of wireless sensor devices;

FIG. 3 illustrates a functional diagram of a wireless sensor device;

Figure 1A:
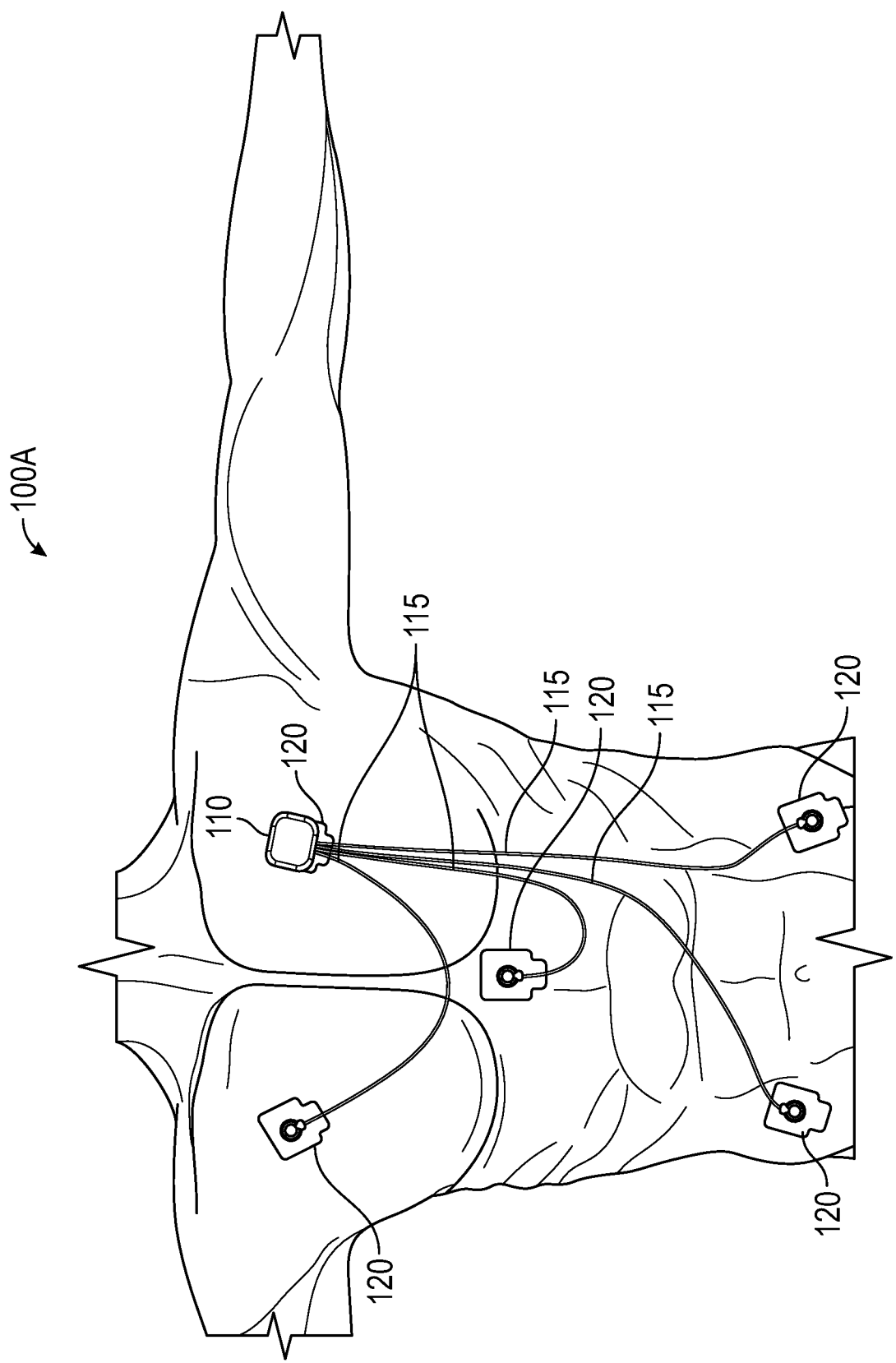
FIG. 1A illustrates one example of a wireless physiological sensing module.

In the drawings, like reference numerals indicate like elements. While the above-identified drawings, which may not be drawn to scale, set forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above those other elements.

As used herein, when an element, component or layer for example is described as being "on" "connected to," "coupled to" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as being "directly on," "directly connected to," "directly coupled to," or "directly in contact with" another element, there are no intervening elements, components or layers for example.

At least some aspects of the present disclosure direct to a wireless sensor device attached to a physiological sensor, for example, an electrocardiography ("ECG") electrode, such that it is mechanically and electrically connected to the sensor and capable of transmitting sensor signal measured by the sensor wirelessly. In some embodiments, the wireless sensor device has a housing having a fastener to connect to a physiological sensor electrically and mechanically. In some embodiments, the wireless sensor device has a housing having a snap fastener female connector to receive a snap fastener male connector of a physiological sensor. In some embodiments, the wireless sensor device can connect to lead wires to receive signals from electrodes. In some other embodiments, the wireless sensor device further includes a near field communication ("NFC") transmitter or transceiver. In some cases, the wireless sensor device can use the NFC transmitter or transceiver to establish wireless communication, or secured wireless communication, within a physiological monitoring system.

At least some aspects of the present disclosure direct to a wireless physiological monitoring system. In some embodiments, the wireless physiological monitoring system includes a wireless sensor device connecting to one or more physiological sensors and a wireless adaptor device configured to pair with the wireless sensor device. The wireless adaptor device may be used to connect to a patient monitor and provide processed or unprocessed data collected by the physiological sensors to the patient monitor. A wireless physiological monitoring system has multiple potential benefits, for example, improved patient comfort and safety, reduced infection risk, reduced false alarms, easier patient transport and handling, increased productivity of nursing/support staff, and/or easier and safer patient ambulation. In some embodiments, the wireless sensor device and the wireless adaptor each includes a NFC transceiver to establish pairing including, for example, secure communications.

FIG. 1A illustrates one example of a wireless physiological sensing module 100A. The sensing module 100A includes a plurality of sensors 120 and a wireless sensor device 110. The plurality of sensors 120 may include a plurality of physiological sensors and other sensors, including, for example, accelerometers, magnetic, motion sensors, temperature sensors, humidity sensors, light sensors or the like. The physiological sensors may include, for example, ECG electrodes, $SpO_2$ sensors, body temperature sensors, blood pressure sensors, acoustical sensors, or the like. In the embodiment illustrated, the wireless sensor device 110 includes a plurality of connectors that are a plurality of wires 115. In some other embodiments, the wireless sensor device 110 includes a plurality of connectors to connect to the plurality of wires 115. In some embodiments, at least some of the plurality of wires are connected to a sensor respectively. In some cases, the wireless sensor device 110 is electrically connected to a sensor 120. In some embodiments, the wireless sensor device 110 is attached to a sensor 120. In some cases, the wireless sensor device 110 is disposable. In some embodiments, the wireless sensor device 110 is configured to receive sensing data from the plurality of sensors 120 and wirelessly transmitting the sensing data to a monitoring system.

In one example embodiment, the sensor device 110 is attached to an ECG electrode placed over the left arm (LA) site. The plurality of wires 115 also connect the sensor device 110 to the right arm (RA), left leg (LL), right leg (RL), and central electrodes 120. In some embodiments, the plurality of sensors 120 is also configured to monitor respiration. In some cases, the wireless sensor device 110 may be powered by a battery (e.g. rechargeable or disposable) or other storage device (e.g. capacitor). In some cases, the wireless sensor device 110 may function continuously or periodically for several days (e.g., 1-5 days) before energy is consumed and sensor device needs to be recharged or discarded. In some cases, the storage device may be recharged by inductive components. In some cases, the wireless sensor device 110 may be powered by energy harvesting components (e.g. light, heat, chemical, movement, vibration).

Figure 1B:
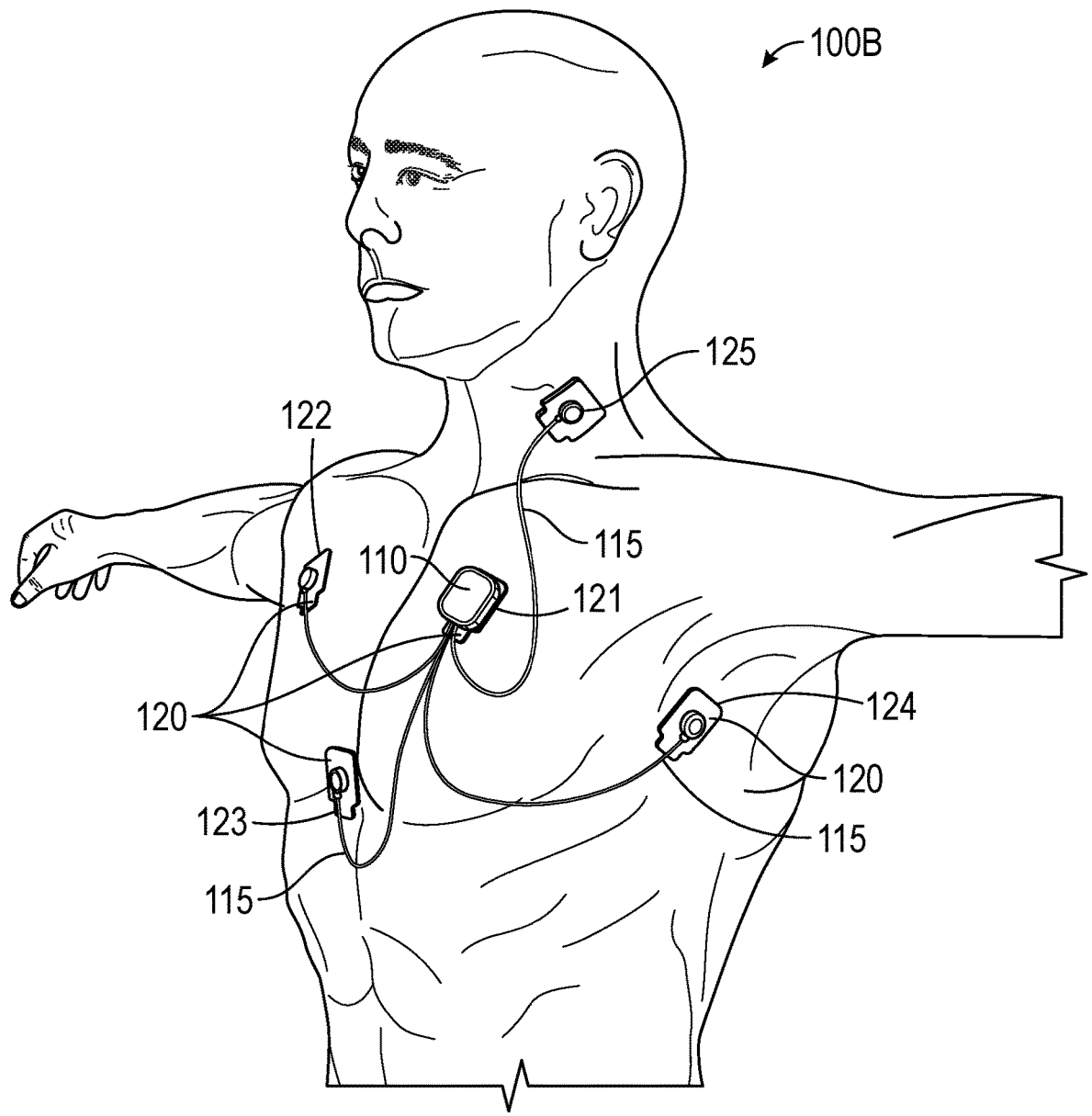
FIG. 1B illustrates another example of a wireless physiological sensing module.

FIG. 1B illustrates another example of a wireless physiological sensing module 100B. The sensing module 100B includes a plurality of sensors 120 and a wireless sensor device 110. In the embodiment illustrated, the wireless sensor device 110 includes a plurality of wires 115. In some other embodiments, the wireless sensor device 110 includes a plurality of connectors to connect to the plurality of wires 115. In some embodiments, at least some of the plurality of wires are connected to a sensor respectively. In some cases, the sensor device 110 is electrically connected to a sensor 120. In some embodiments, the sensor device 110 is attached to a sensor 120. In some embodiments, the sensor device 110 is configured to receive sensing data from the plurality of sensors 120 and wirelessly transmitting the sensing data to a monitoring system.

In one example embodiment, the sensor device 110 is attached to a sensor 121 placed over the left arm (LA) site. One wire 115 connects the sensor device 110 to a sensor 122 placed on the right arm (RA) for ECG and respiration measurement. One wire 115 connects the sensor device 110 to an oximeter sensor ($SpO_2$) 123 placed over a person's sternum. One wire 115 connects the sensor device 110 to a temperature sensor 124 placed under the armpit (axillary temperature). One wire 115 connects the sensor device 110 to an acoustic sensor 125 place over the trachea, for example, to measure lung sounds, respiration, voice, or the like.

Figure 1C:
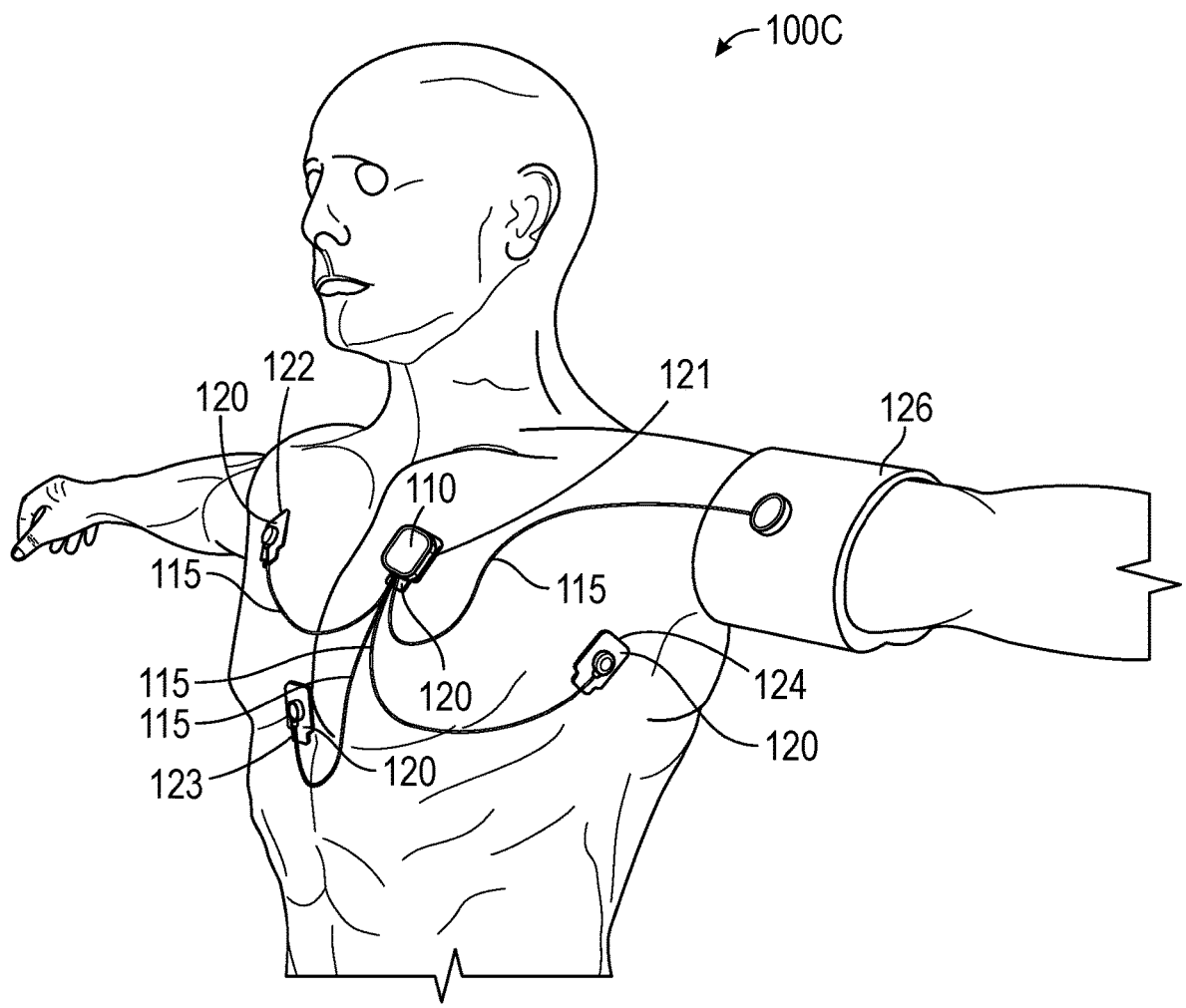
FIG. 1C illustrates another example of a wireless physiological sensing module.

FIG. 1C illustrates another example of a wireless physiological sensing module 100C. The sensing module 100C includes a plurality of sensors 120 and a wireless sensor device 110. In the embodiment illustrated, the wireless sensor device 110 includes a plurality of wires 115. In some other embodiments, a wireless sensor device 110 includes a plurality of connectors to connect to the plurality of wires 115. In some embodiments, at least some of the plurality of wires are connected to a sensor respectively. In some cases, the sensor device 110 is electrically connected to a sensor 120. In some embodiments, the sensor device 110 is attached to a sensor 120. In some cases this electrical connection may be via fiber optic cable or some other non-conductive means. In some cases, the sensor device is wirelessly connected to a sensor 120, via a wireless communication interface, for example, ANT protocol, Bluetooth low energy, or the like. In some embodiments, the sensor device 110 is configured to receive sensing data from the plurality of sensors 120 and wirelessly transmitting the sensing data to a monitoring system. In some embodiments, a sensor 120 is configured to receive sensing data from another sensor(s) and transmit the data to the sensor device 110 or yet another sensor. In some cases, the data may be sent over a digital bus (e.g. I2C, SPI). In some cases, this data may be sent utilizing fiber optic cable. In some cases this data may be sent wirelessly.

In one example embodiment, the sensor device 110 is attached to a sensor 121 placed over the left arm (LA) site. One wire 115 connects the sensor device 110 to a sensor 122 placed on the right arm (RA) for ECG and respiration measurement. One wire 115 connects the sensor device 110 to an oximeter sensor (SpO$_2$) 123 placed over a person's sternum. One wire 115 connects the sensor device 110 to a temperature sensor 124 placed under the armpit (axillary temperature). One wire 115 connects the sensor device 110 to a non-invasive blood pressure device 126. The blood pressure measure device 126 contains a battery activated pump. The sensor device 110 would initiate the blood pressure measurement and collect blood pressure measurement.

Figure 2C:
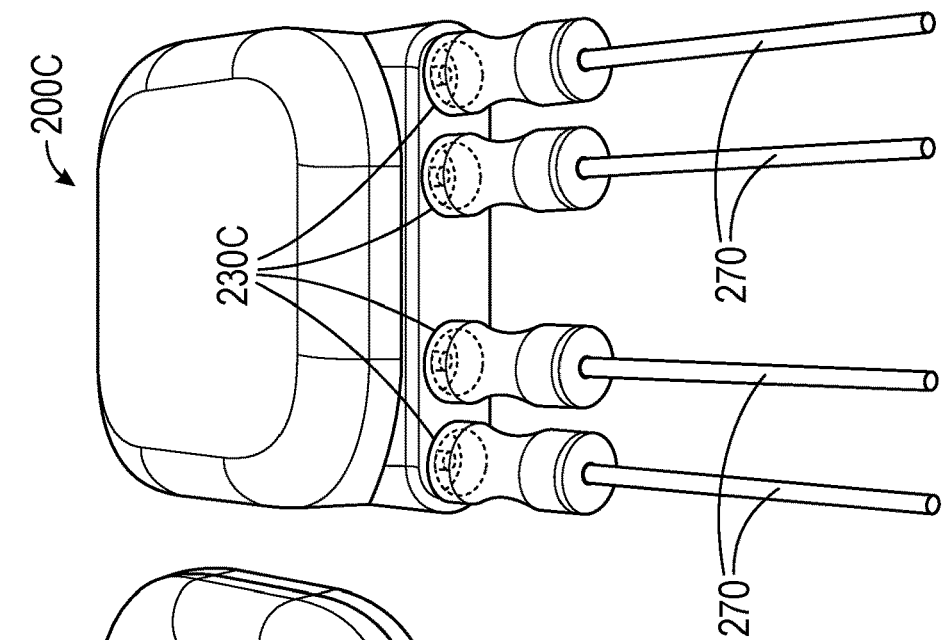
Figure 2B:
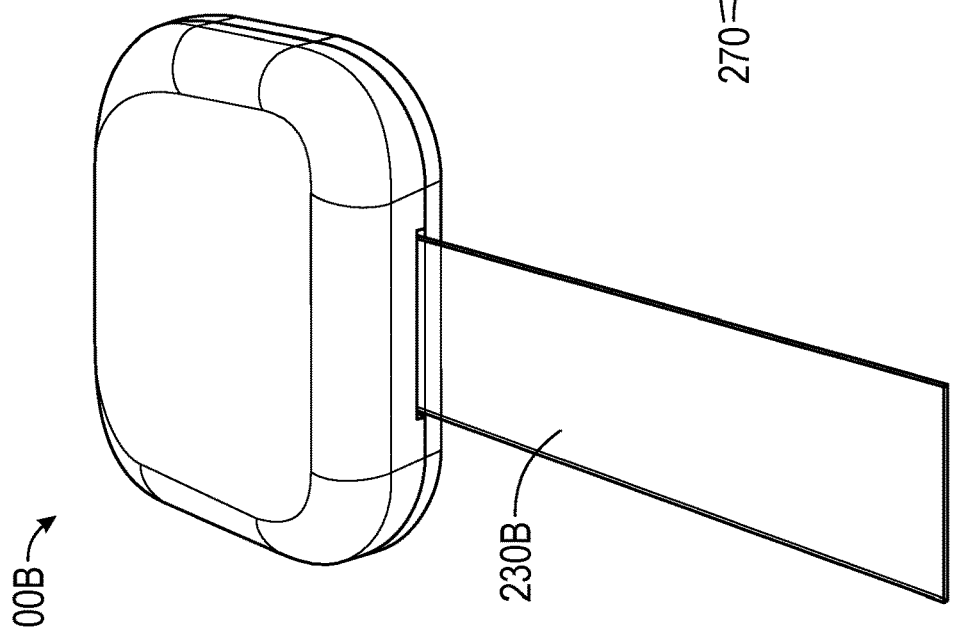
Figure 2A:
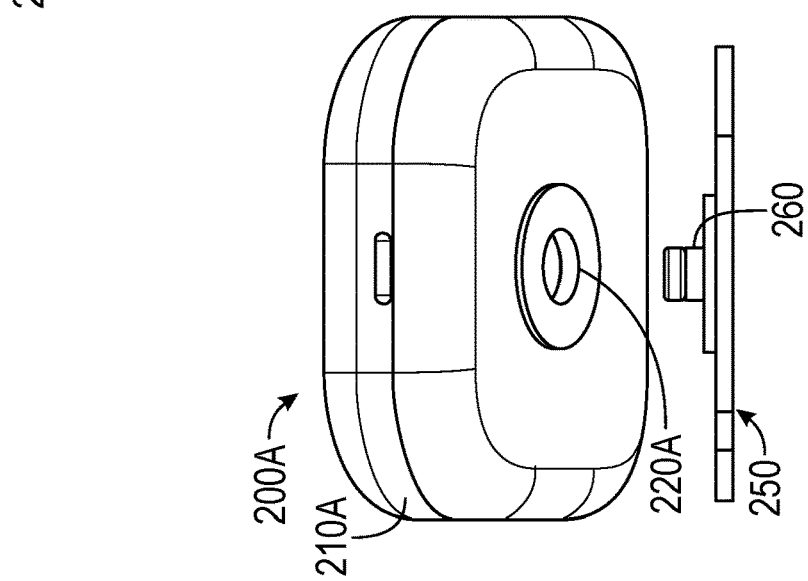

FIGS. 2A-2H illustrate several example embodiments of wireless sensor devices. FIG. 2A illustrates one example of a wireless sensor device 200A. The wireless sensor device 200A has a housing 210A, which is a rounded rectangular shape. The housing 210A includes a snap fastener female connector 220A. The female connector 220A is configured to receive a snap fastener male connector 260 of a sensor 250. The female connector 220A and the male connector 260 maintain an electrical connection. In addition, the female connector 220A and the male connector 260 maintain a mechanical connection and allow swivel in the connection. In some embodiments, the housing 210A may include other types of fasteners to connect to a sensor electrically and mechanically, for example, DIN 42802 compliant touch-proof connectors or custom connectors. In some embodiments, the housing 210A has a cross-section area no greater than 45 mm×45 mm and a height no greater than 30 mm when the housing is rectangular, circular, or some combination of the two (e.g., the housing illustrated in FIGS. 2D and 2G). In such embodiments, the housing 210A is small enough to snap to a sensor attached to a person's skin without causing the sensor to fall off. In some cases, the housing 210A are smooth with rounded edges to prevent clothing or other objects snagging and/or pulling off the wireless sensor device. In some cases, the wireless sensor device 200A is light weight. In some cases, the wireless sensor device 200A is less than 15 grams. In some cases, the wireless sensor device 200A is less than 30 grams. In some embodiments, the housing 210A has a size no greater than 150 mm long and a 25 mm diameter when the housing is cylindrical (e.g., the housing illustrated in FIG. 2E). In such embodiments, the housing 210A is small enough to snap to a sensor attached to a person's skin without causing the sensor to fall off. In some embodiments, the housing 210A may be made from a polymer material, for example, Acrylonitrile Butadiene Styrene (ABS), Polycarbonates (PC), or Polypropylene (PP).

In some embodiments, the signal collected by the wireless sensor device 200A may be analog or digital. In some cases, the wireless sensor device 200A collect original sensed format (e.g. analog) replicating the original signals from the sensor measurement. In some other cases, the wireless sensor device 200A may process the sensor data and transmit the processed sensor data, which may be analog or digital.

Figure 2F:
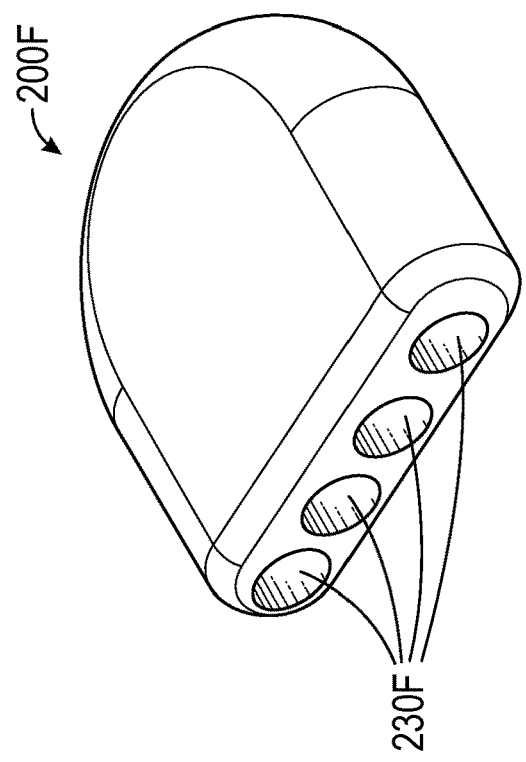
Figure 2E:
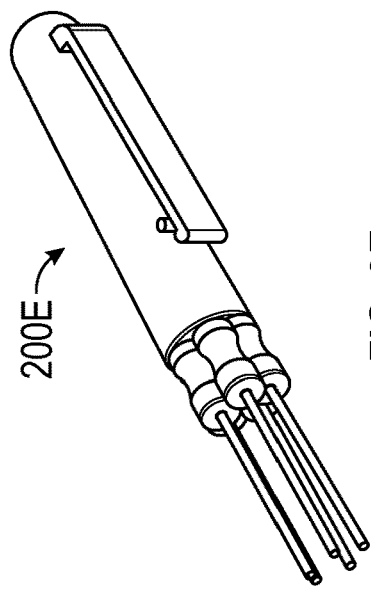
Figure 2D:
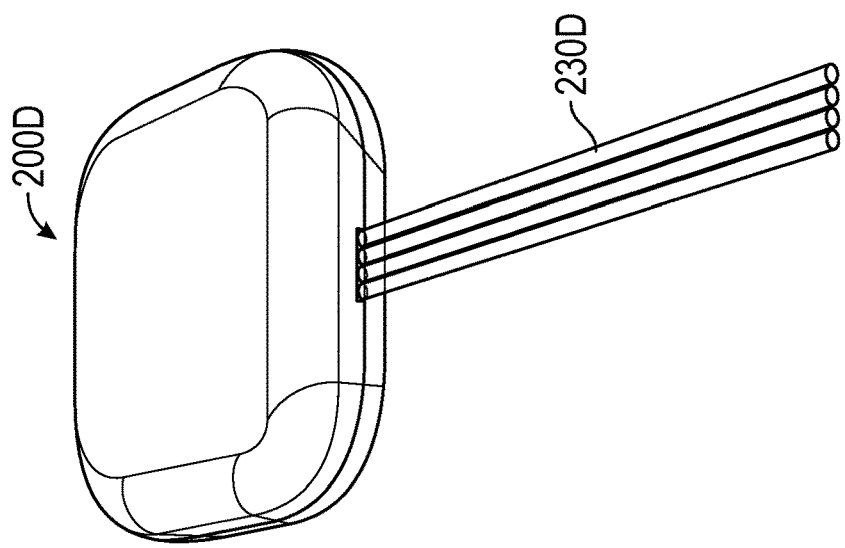

FIGS. 2B-2D illustrate some examples of wireless sensor devices with different wire configurations. FIG. 2B illustrates a wireless sensor device 200B includes a flat cable 230B that is configured to connect to a plurality of physiology sensors. FIG. 2C illustrates a wireless sensor device 200C includes a plurality of universal connectors 230C configured to connect to a plurality of wires 270. FIG. 2D illustrates a wireless sensor device 200D includes a plurality of cable wires 230D configured to connect to a plurality of physiology sensors.

A wireless sensor device may have various shapes, for example, rectangular, circular, cylindrical, a combined shape, or the like. FIGS. 2E-2G illustrate some examples of wireless sensor devices with different shapes. FIG. 2E illustrates a wireless sensor device 200E has a shape of pen. FIG. 2F illustrates a wireless sensor device 200F has a combination shape of a rectangle and half circle. The wireless sensor device 200F includes a plurality of connectors 230F. FIG. 2G illustrates a wireless sensor device 200G has a circular shape. The wireless sensor device 200G includes a plurality of wires 230G.

FIG. 2H illustrates one example embodiment of a wireless sensor device 200H. In the example illustrated, the wireless sensor device 200H includes two parts—a base component 210H that can attach to a sensor and a removable component 220H. In some cases, the base component 201H includes a plurality of connectors 230H. In one case, the base component 210H may contain electronics that are disposable (e.g. battery), while the removable component 220H may contain electronics that are to be re-used. In another case, the base component 210H may contain electronics that are reusable or disposable and the removable component 220H may contain a rechargeable battery or a disposable battery. In yet another case, the base component 210H may contain electronics and a battery and the removable component 220H may contain electronics, processor, and/or memory used to associate the sensor device with another device.

FIG. 3 illustrates a functional diagram of a wireless sensor device 300. In one embodiment, the wireless sensor device 300 includes a housing 310, a mechanical/electrical connector 315, and a wireless transceiver 320. The wireless sensor device 300 can use any configurations of wireless sensor device described herein. In one embodiment, the wireless transceiver 320 can transmit and receive data in multiple radio bands, for example, 802.11 a/b/c/g/n, medical radio band, near field communication protocol, Bluetooth, Bluetooth Low Energy, ultra-wideband (UWB) or the like. In another embodiment, the wireless transceiver 320 can transmit and/or receive data via cellular connection. In another embodiment, the wireless transceiver 320 can transmit and/or receive data utilizing Bluetooth or Bluetooth Low Energy.

In some embodiments, the wireless sensor device 300 optionally includes an NFC transceiver 325. The NFC transceiver 325 can use a communication specification includes but is not limited to the set of standard protocols defined by the NFC Forum industry association. In some embodiments, the wireless sensor device 300 optionally includes a physiological sensing component 330, which can include one or more sensing components, for example, a sensing component for body temperature, blood pressure, respiration, heart sound, lung sound, and the like. In some embodiments, the wireless sensor device 300 includes one or more motion sensing components 335, for example, such as an accelerometer, gyroscope, or the like. In some embodiments, the wireless sensor device 300 includes one or more environmental sensing component, for example, a sensing component for humidity, temperature, barometric pressure, and the like.

Figure 4:
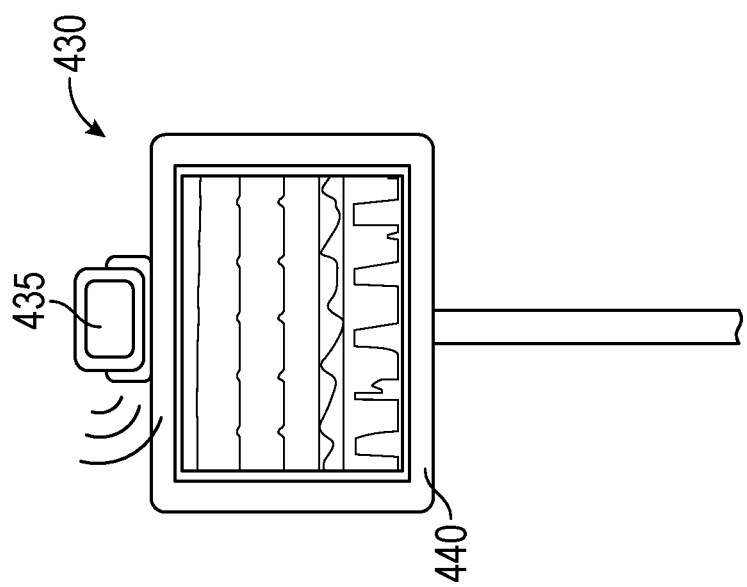
FIG. 4 illustrates one example of a wireless physiological system including a wireless physiological sensing module and a monitoring module.
Figure 4:
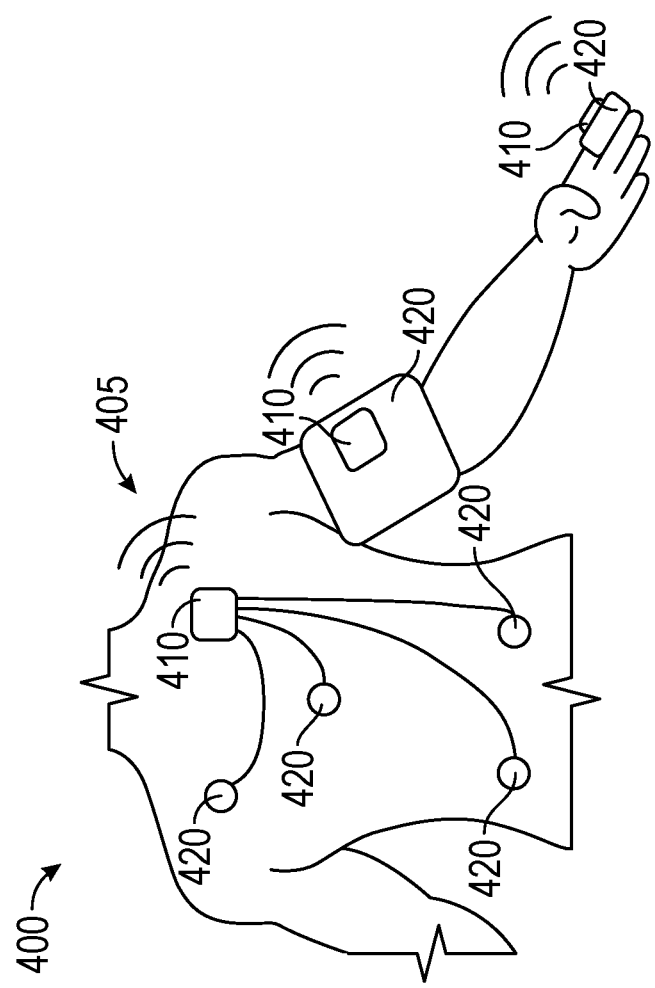

FIG. 4 illustrates one example of a wireless physiological system 400 including a wireless physiological sensing module 405 and a monitoring module 430. The wireless physiological sensing module 405 includes a plurality of wireless sensor devices 410 and a plurality of sensors 420. The wireless sensor device 410 can use any configuration of wireless sensor device described herein. The monitoring module 430 includes a wireless adaptor device 435 and a physiological monitor 440. In some embodiments, the wireless adaptor device 435 is connected to the physiological monitor 440 via a cable.

In some embodiments, the wireless adaptor device 435 is connected to the physiological monitor. In some cases, the connection is designed to be retrofitting to a conventional physiology monitor, for example, retrofitting to existing data ports for a patient monitor. In some implementations, the connection is by a cable connecting to one or more sensor ports on the physiological monitor. In some implementations, the connection is to a data port (e.g. USB, Serial, Ethernet, etc.) on the physiological monitor. In some implementations, the connection is by an input connector either internal or external to the physiological monitor (e.g. accessory port). In some implementations, the connection is integrated directly into the circuitry within the physiological monitor (e.g. PCB) or the physiological monitor's accessories. In some cases, when the wireless adaptor device 435 is disconnected from the physiological monitor, the wireless adaptor device may communicate with a local area network (e.g. WiFi). In some cases, the wireless adaptor device 435 can be portable with a patient and moved with the patient to different locations. The wireless adaptor device 435 is configured to wirelessly connect to the wireless sensor device 410 to one-way or two-way communication to receive sensing data and transmit commands. In some embodiments, the wireless sensor device 410 is configured to pair with the wireless adaptor device 435 via NFC communication.

In some cases, the wireless adaptor device 435 and the wireless sensor device 410 may communicate via the NFC communication to perform a series of set-up operations. In some embodiments, the wireless adaptor device 435 may interrogate the wireless sensor device 410 via an electromagnetic field and supply a part of or all power to the wireless sensor device 410 via the electromagnetic field during the set-up operations. The wireless adaptor device 435 may transmit an activation command to the wireless sensor device 410 via NFC. In one embodiment, the wireless adaptor device 435 may receive the wireless identification of the wireless sensor device 410 via the NFC communication. Next, the wireless adaptor device 435 may use the wireless identification to establish a wireless connection with the wireless sensor device 410. The wireless identification may be any data or information that can identify the wireless sensor device 410. For example, the wireless identification may be an IP (i.e., internet protocol) address, a patient identification, a device identification, or the like. The wireless identification may include security related data for wireless connection, for example, a pass code, the type of security, encryption keys, or the like. The wireless identification may be a combination of multiple pieces of data, for example, a combination of a device identification and a pass code to authenticate the wireless sensor device and allow secured connection.

In some embodiments, the wireless sensor device 410 may transmit patient information to the wireless adaptor device 435 via NFC communication. In some embodiments, the wireless sensor device 410 may transmit device information (e.g. hardware identifier, model, hardware version, firmware version, activated features, manufacturing lot and date, etc.) and/or configuration information (e.g., access point ID, SSID, BSSID, radio band, encryption key, channel, password, activated features, restrictions, etc.) to the wireless adaptor device 435 via the NFC communication. In some embodiments, the wireless sensor device 410 may transmit patient information and patient limits/restrictions (e.g., patient identification number, location restrictions, sensor limits, etc.) to the wireless adaptor device 435 via the NFC communication.

Figure 5A:
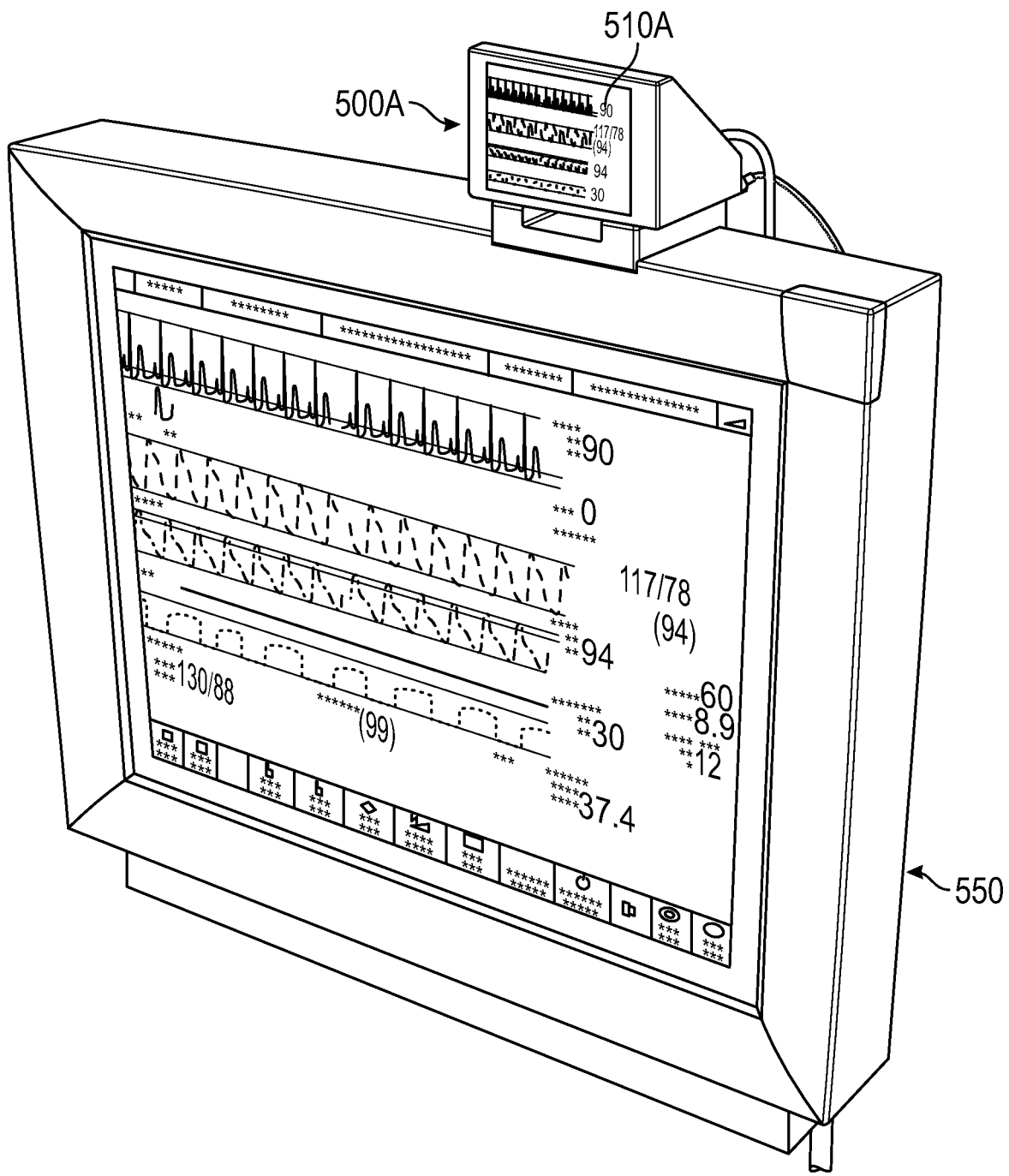
FIGS. 5A-5C illustrates some example embodiments of wireless adaptor devices.
Figure 5C:
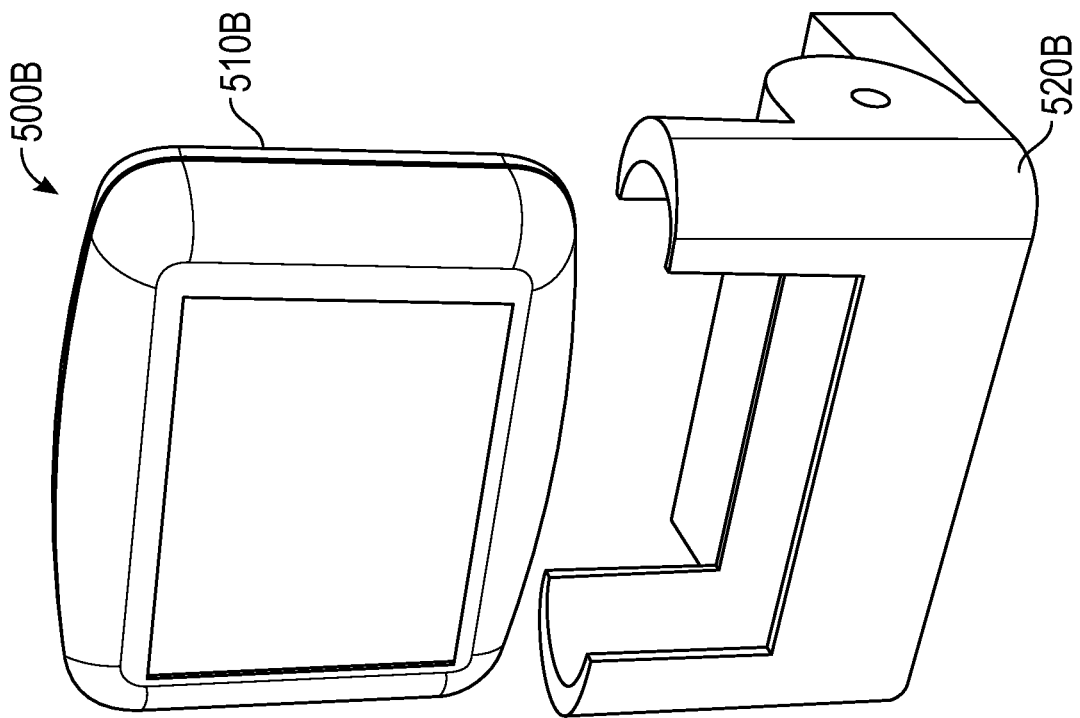
Figure 5B:
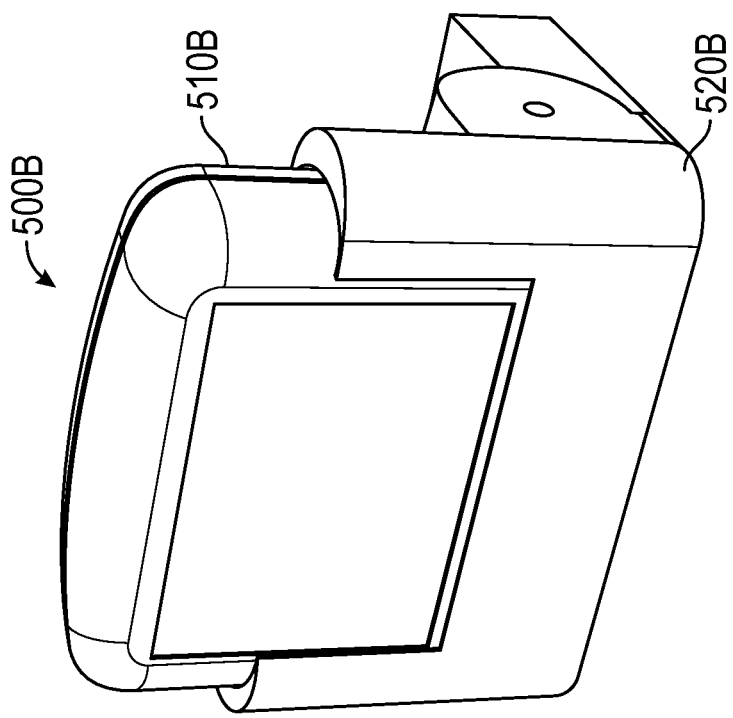

FIGS. 5A-5C illustrates some example embodiments of wireless adaptor devices. FIG. 5A illustrates one embodiment of a wireless adaptor device 500A. In some embodiments, the wireless adaptor device 500A includes a processing unit, a wireless transceiver, an optional NFC transceiver, and a connector to connect to a physiological monitor 550. In some embodiments, the connector is a set of wires. In some other embodiments, the connector is a wireless connection. In some cases, the wireless adaptor device 500A may be powered via a connection with the physiological monitor. In some cases, the wireless adaptor device 500A may be powered by a battery or an external AC/DC power supply. In the embodiment illustrated, the wireless adaptor device 500A includes a display or a touch screen 510A. In some cases, the display or the touch screen 510A has a horizontal display.

In some cases, the wireless adaptor device 500A may transmit analog or digital data to the physiological monitor 550. In some cases, the information provided to the physiological monitor 550 may be presented in the original sensed format (e.g. analog) replicating the original signals collected from sensors, for example, ECG electrodes. In some cases, the information provided to the physiological monitor 550 may be presented in a processed format based on the original sensed format (e.g. filtered, converted).

FIGS. 5B and 5C illustrate another embodiment of a wireless adaptor device 500B, which has a wireless component 510B and a docking component 520B. In such embodiments, the wireless component 510B can be removed from the docking component 520B, as illustrated in FIG. 5C. In some cases, the wireless adaptor device 500B, the wireless component 510B, and/or the docking component 520B may include a user interface, for example, a display, a touch screen, one or more buttons, a microphone, a combination of user interface components, or the like. In some cases, the wireless component 510B and the docking component 520B may each include a processing unit and means for communication information between the two components (e.g. electrical, optical, inductive, wireless etc.). In some cases, the wireless adaptor device 500B or the wireless component 510B may include a disposable covering (e.g. sleeve to prevent transmission of infectious materials or prevent bodily fluids from entering the device) which still allow for user interaction with the device. In some cases, the wireless component 510B can be portable with a patient and transported with the patient.

Figure 6:
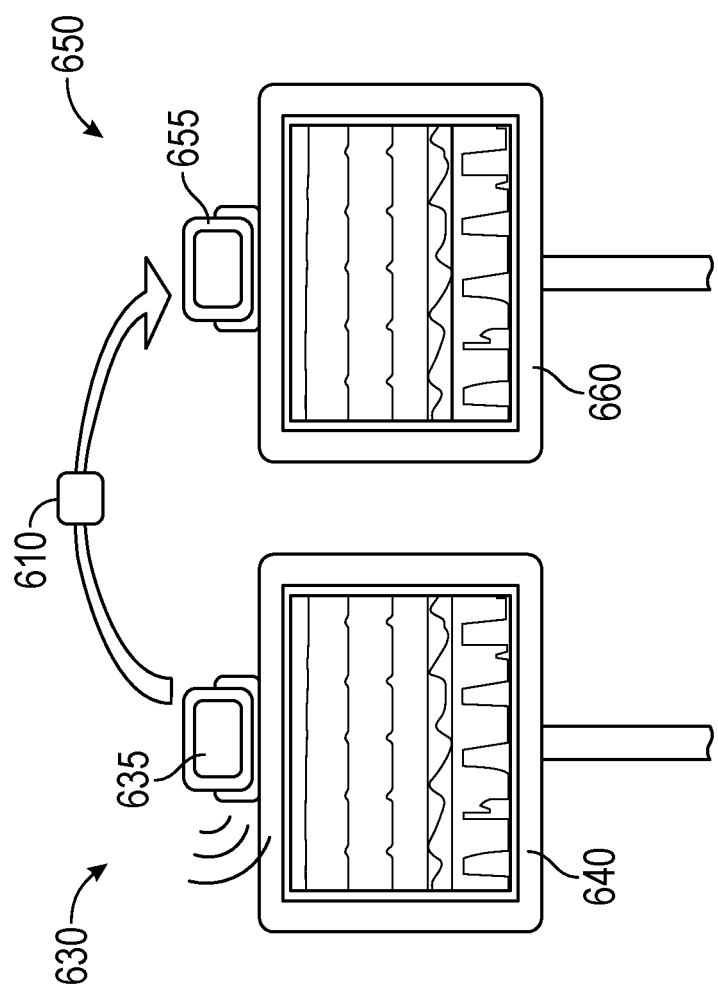
FIG. 6 illustrates one example of a wireless physiology monitoring system.
Figure 6:
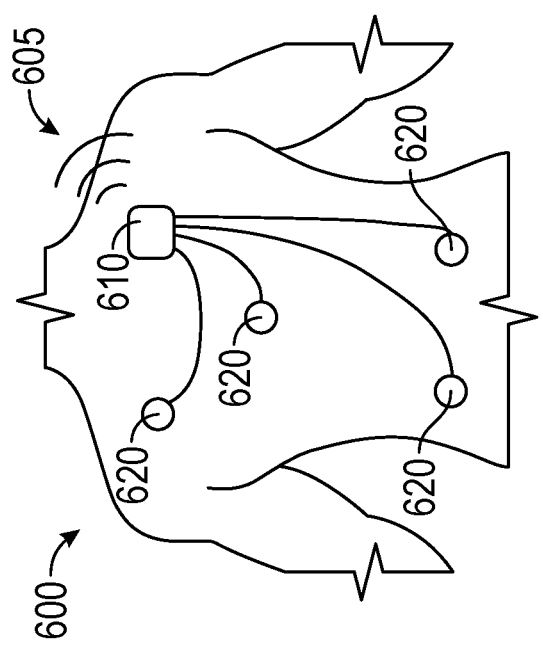

In some cases, a wireless sensor device can send sensor data to one or more wireless adaptor devices. In some cases, a wireless adaptor device can receive sensor data from one or more wireless sensor devices. FIG. 6 illustrates one example of a wireless physiology monitoring system 600. In this example, the wireless physiology monitoring system 600 includes a wireless physiological sensing module 605, a first monitoring module 630, and a second monitoring module 650. The wireless physiological sensing module 605 includes a plurality of wireless sensor devices 610 and a plurality of sensors 620. The wireless sensor device 610 can use any configuration of wireless sensor device described herein. The monitoring module 630 includes a wireless adaptor device 635 and a physiological monitor 640. The monitoring module 650 includes a wireless adaptor device 655 and a physiological monitor 660. The wireless adaptor device 635 and/or 655 is configured to wirelessly connect to the wireless sensor device 610 to one-way or two-way communication to receive sensing data and transmit commands. In some embodiments, the wireless sensor device 610 is configured to pair with the wireless adaptor device 635 and/or 655 via NFC communication.

In some embodiments, a wireless adaptor device is located on or near every physiological monitor in the facility, where each wireless adaptor device must be paired with the patient's sensor device as the patient is moved throughout the facility. For example, the wireless sensor device is paired with the wireless adaptor device or the bedside monitor while the patient is in the room; the wireless sensor device is paired with the transport monitor when the patient is being moved to another location; and the wireless sensor device is paired with the destination physiological monitor upon the patients arrival at a new location. In some other embodiments, a docking component is located on or near every physiological monitor in the facility and a wireless component is given to a patient upon admission. Such wireless component moves with the patient, being inserted into a respective docking component on a physiological monitor as necessary as the patient moves throughout the facility, for example, inserted in the bedside monitor docking component while the patient is in the room, inserted into the transport monitor docking component when the patient is being moved to another location, or inserted into the destination physiological monitor docking component upon the patient arrival to a new location.

Figure 7A:
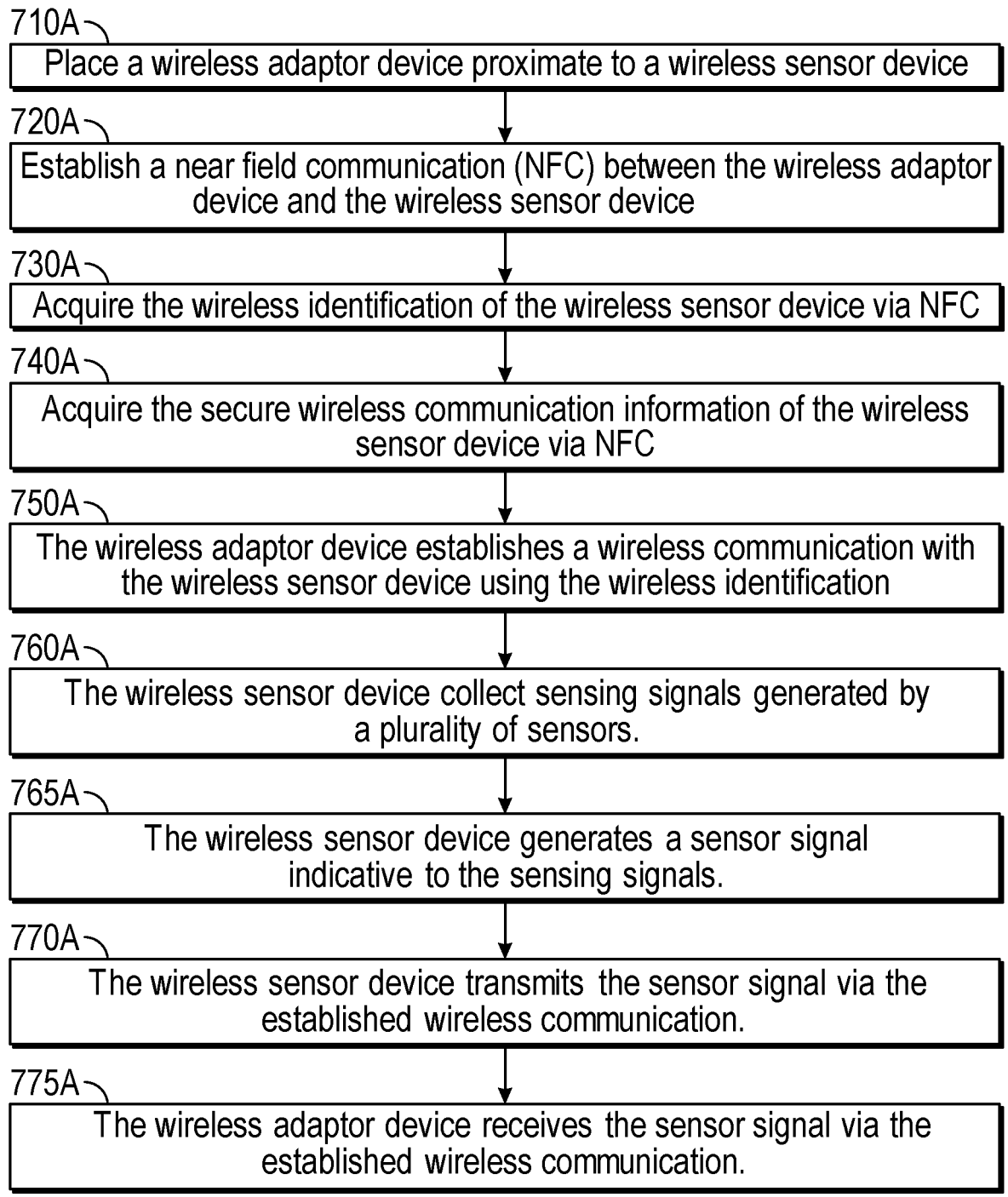
FIG. 7A is one example flow diagram of a wireless physiological monitoring system.

FIG. 7A is one example flow diagram of a wireless physiological monitoring system using any embodiment of wireless sensor device and wireless adaptor device described herein. First, place a wireless adaptor device in close proximity to a wireless sensor device or vice versa (step 710A). Establish a near field communication (NFC) between the wireless adaptor device and the wireless sensor device (step 720A). Acquire the wireless identification of the wireless sensor device via NFC (step 730A). In some cases, only the wireless component of the wireless adaptor device may be placed in close proximity to the wireless sensor device. Optionally, the wireless adaptor device acquires the secure wireless communication information of the wireless sensor device via NFC (step 740A). The wireless adaptor device establishes a wireless communication with the wireless sensor device using the wireless identification (step 750A). Next, the wireless sensor device collects sensing signals generated by a plurality of sensors (step 760A). The wireless sensor device generates a sensor signal indicative to the sensing signals (step 765A). The wireless sensor device transmits the sensor signal via the established wireless communication (step 770A). The wireless adaptor device receives the sensor signal via the established wireless communication (step 775A).

Figure 7B:
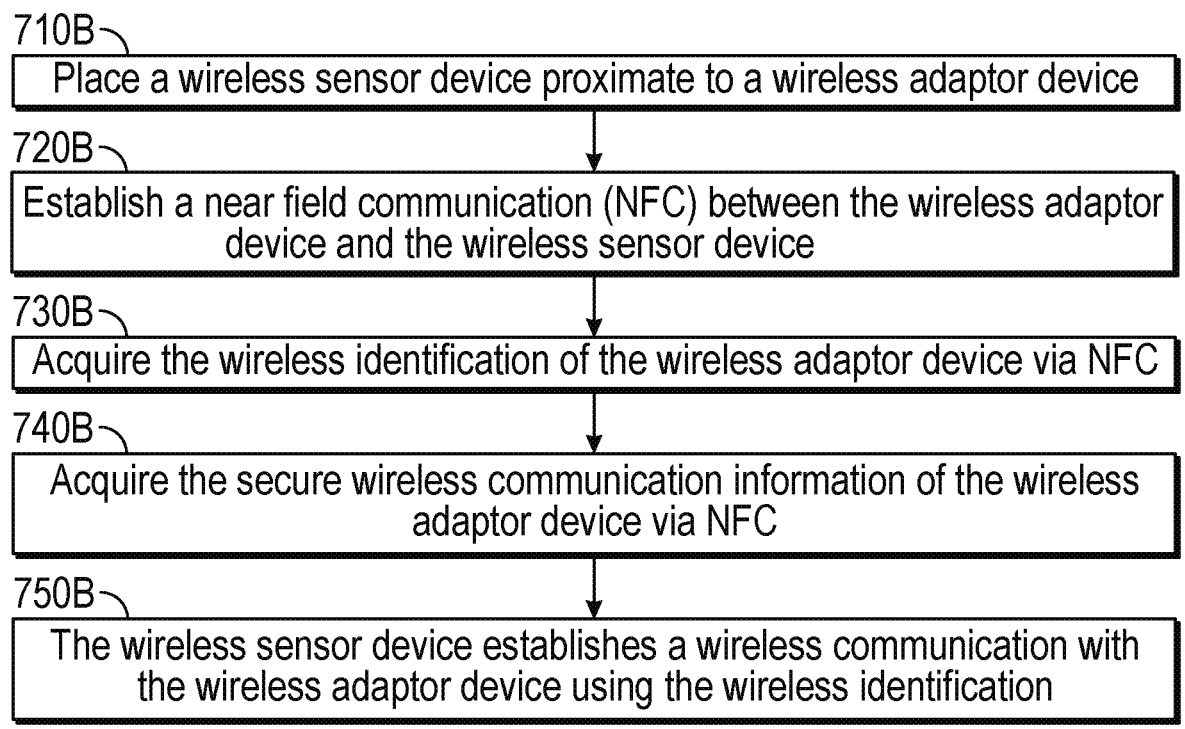
FIG. 7B is another example flow diagram of a wireless physiological monitoring system.

FIG. 7B is another example flow diagram of a wireless physiological monitoring system using any embodiment of wireless sensor device and wireless adaptor device described herein. First, place a wireless sensor device in a close proximity to a wireless adaptor device or vice versa (step 710B). Establish a near field communication (NFC) between the wireless adaptor device and the wireless sensor device (step 720B). The wireless sensor device acquires the wireless identification of the wireless adaptor device via NFC (step 730B). In some cases, only the removable component of the wireless sensor device may be placed in close proximity to the wireless adaptor device. Optionally, the wireless sensor devices acquires the secure wireless communication information of the wireless adaptor device via NFC (step 740B). The wireless sensor device establishes a wireless communication with the wireless sensor device using the wireless identification (step 750B). The wireless physiological monitoring system may include one or more other steps as described in FIG. 7A.

Figure 7C:
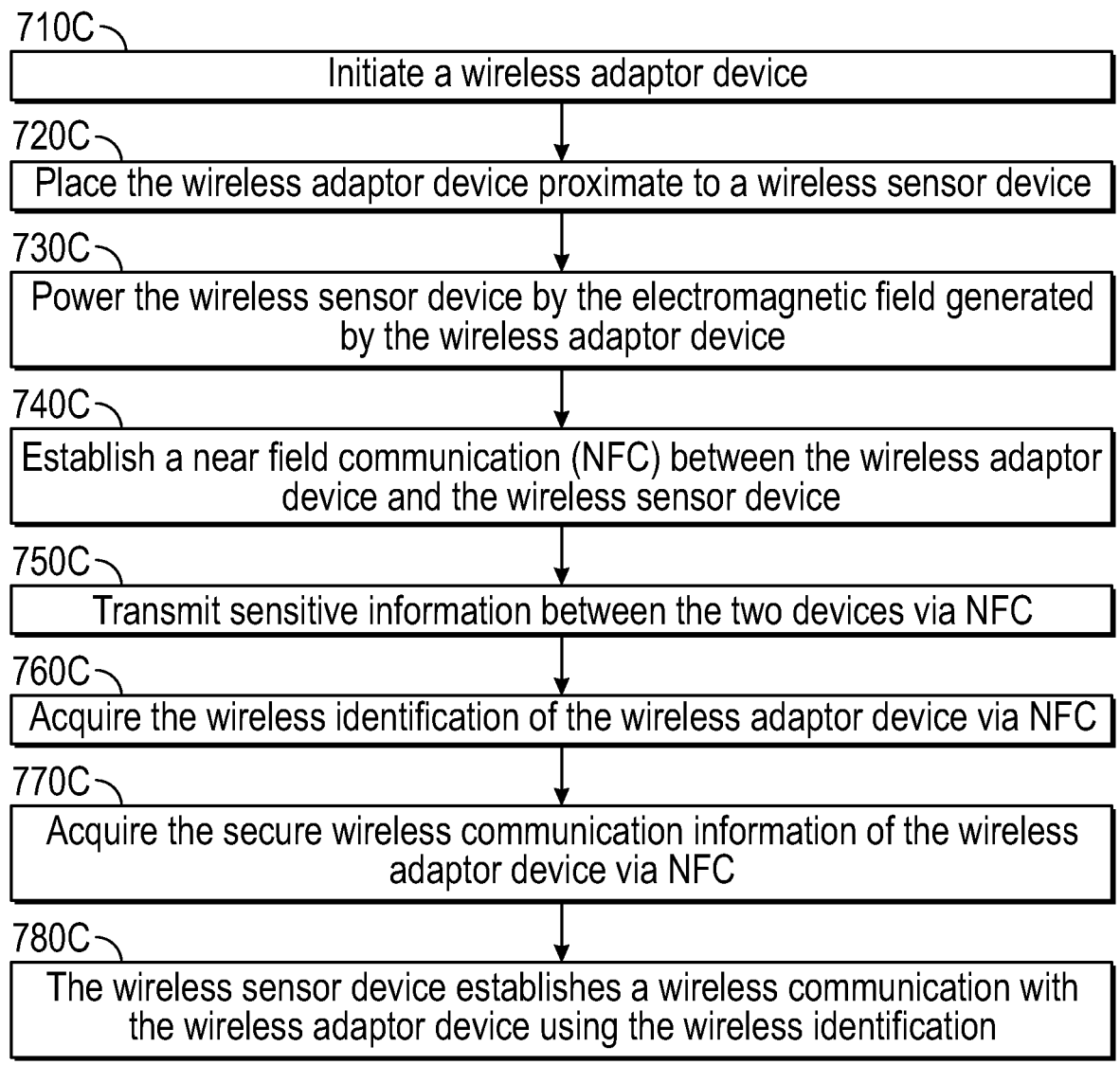
FIG. 7C is yet another example flow diagram of a wireless physiological monitoring system.

FIG. 7C is yet another example flow diagram of a wireless physiological monitoring system using any embodiment of wireless sensor device and wireless adaptor device described herein. First, initiate a wireless adaptor device (step 710C). Place the wireless adaptor device proximate to a wireless sensor device (step 720C). Optionally, power the wireless sensor device by the electromagnetic field generated by the wireless adaptor device (step 730C). Establish a near field communication (NFC) between the wireless adaptor device and the wireless sensor device (step 740C). Transmit and receive sensitive information between the two devices via NFC (step 750C). The wireless sensor device acquires the wireless identification of the wireless adaptor device via NFC (step 760C). Optionally, the wireless sensor device acquires the secure wireless communication information (e.g., encryption information) of the wireless adaptor device via NFC (step 770C). The wireless sensor device establishes a wireless communication with the wireless adaptor device using the wireless identification (step 780C). In some cases, such wireless communication is a secured wireless communication. The wireless physiological monitoring system may include one or more of other steps as recited in FIG. 7A.

EXAMPLES

TABLE 1

EQUIPMENT AND COMPONENTS FOR EXAMPLE 1

| Item | Description | Source/Supplier |
|---|---|---|
| Patient Simulator #1 | Fluke Biomedical ProSim 8 Vital Signs Simulator | Fluke Biomedical |
| Sensor Device #1 | Sensor printed circuit board (PCB) containing a HC1100 wireless sensor IC, CP251525 Lithium | PCB: HMicro Inc. Battery: PowerStream Leads: 3M Company |

TABLE 1-continued

EQUIPMENT AND COMPONENTS FOR EXAMPLE 1

| Item | Description | Source/Supplier |
| --- | --- | --- |
| Wireless Adapter #1 | Battery, and YMDLW5S lead wire Adapter PCB containing a HC1100 wireless sensor IC, monitor cable (to ECG port on physiological monitor). | PCB: HMicro Inc. Cable: AMC&E |
| Physiological Monitor | INTELLIVUE MP70 | Philips Healthcare |
| Sensor Device #1 | Sensor printed circuit board (PCB) containing a HC1100 wireless sensor IC, CP251525 Lithium Battery, and YMDLW5S lead wire | PCB: HMicro Inc. Battery: PowerStream Leads: 3M Company |

Example 1

Wireless ECG

The Wireless ECG system of Example 1 was configured and connected as follows, which is a system similar to the one illustrated in FIG. 4. The Physiological Monitor was powered on. The Physiological Monitor was configured for leads I, II, III, and V. The Wireless Adaptor #1 device was connected to the Physiological Monitor. The Wireless Adaptor #1 device was powered on. The lead wires connects the Sensor Device #1 to the Patient Simulator: RA, LA, LL, RL, V. The Patient Simulator #1 was powered on. The Patient Simulator #1 was configured to an ECG of 60 bpm (beats per minute). The Sensor Device #1 was powered on. The signal output from the Patient Simulator #1 was wirelessly transmitted from the Sensor Device #1 to the Wireless Adaptor #1 and the signal was observed and confirmed on the Physiological Monitor. The output of the Patient Simulator #1 was varied and the output of the Wireless Adaptor #1 with same values within error range was observed and confirmed on the Physiological Monitor.

TABLE 2

EQUIPMENT AND COMPONENTS FOR EXAMPLE 2

| Item | Description | Source/Supplicer |
| --- | --- | --- |
| Patient Simulator #2 | Biomedical ProSim 8 Vital Signs Simulator | Fluke Biomedical |
| Sensor Device #2 | Sensor printed circuit board (PCB) containing a HC1100 wireless sensor IC, CP251525 Lithium Battery, and temperature cable to the simulator. | PCB: HMicro Inc. Battery: PowerStream Cable: Fluke Biomedical |
| Wireless Adapter #2 | Adapter PCB containing a HC1100 wireless sensor IC, monitor cable (to temperature port on physiological monitor). | PCB: HMicro Inc. Cable: AMC&E |
| Physiological Monitor | INTELLIVUE MP70 | Philips Healthcare |

Example 2

Wireless Patient Temperature Sensor

The Wireless Patient Temperature Monitoring System of Example 2 was configured and connected as follows, which is a system similar to the one illustrated in FIG. 4. The Physiological Monitor was powered on. The Physiological Monitor was configured for temperature input. The Wireless Adaptor #2 device was connected to the Physiological Monitor. The Wireless Adaptor #2 device was powered on. The temperature input cable connected the Sensor Device #2 to the temperature port of the Patient Simulator. The Patient Simulator #2 was powered on and the temperature parameters were configured (e.g. temperature range from 30-42 degrees C., 0.5 degree increments). The Sensor Device #2 was powered on. The signal output from the Patient Simulator #2 as wirelessly transmitted from the Sensor Device #2 to the Wireless Adapter #2 and the signal was observed and confirmed on the Physiological Monitor. The temperature output of the Patient Simulator #2 was varied and the output of the Wireless Adaptor #2 with same values within error range was observed and confirmed on the Physiological Monitor.

TABLE 3

EQUIPMENT AND COMPONENTS FOR EXAMPLE 3

| Item | Description | Source |
| --- | --- | --- |
| Sensor Device #3 | PCB containing a K20DX256VLH7 microcontroller, NT3H1201 I2C NFC IC, NFC antenna, and CP251525 Lithium Battery | Microcontroller: NXP Freescale NFC IC: NXP Antenna: custom wire antenna Battery: Powerstream |
| Wireless Adapter #3 | PCB containing a K20DX256VLH7 microcontroller, PN532 NFC Controller IC, NFC antenna, USB 5 V power supply | Micrcontroller: NXP Freescale NFC IC: NXP Antenna: custom PCB antenna |

Example 3

Near Field Communication (NFC) Pairing of Devices

The wireless NFC pairing of the Sensor Device #3 and Wireless Adaptor #3 Patient was demonstrated as follows, which is a system similar to the one illustrated in FIG. 4. The Wireless Adaptor #3 device was powered on. The "Pair" option on the Wireless Adaptor #3 was selected. The Sensor Device #3 was not powered up. The Sensor Device #3 was physically placed over the NFC antenna of the Wireless Adaptor #3. Alternatively, Wireless Adaptor #3 was physically placed over the NFC antenna of the Sensor Device #3. The Wireless Adaptor #3 powered the NFC circuit in the Sensor Device #3. The Wireless Adaptor #3 received the Sensor Device #3 information and sends configuration information to the Sensor Device #3. Information from the Sensor Device #3 to the Wireless Adapter #3 included device and manufacturing identification. Information from the Wireless Adapter #3 to the Sensor Device #3 included radio communication information and patient identification information. The Wireless Adapter #3 reads the information received from the Sensor Device #3 and displays the information on a touch screen user interface for confirmation. The Sensor Device #3 was then powered up. The Sensor Device #3 reads the configuration information from NFC circuit memory, validates the information, and sets applicable internal variables accordingly. The configuration information confirmed through reading from serial port of the Sensor Device.

Exemplary Embodiments

Item A1. A wireless sensor device to connect to a supporting physiological sensor, comprising:
a housing having a fastener, the fastener configured to mechanically and electrically connect to the supporting physiological sensor,
a wireless transceiver, and
a plurality of connectors, each connector configured to connect to a sensor,
wherein the wireless sensor device is configured to receive sensing signals from a plurality of sensors via the plurality of connectors and from the supporting physiological sensor and wirelessly transmit a sensor signal indicative to the received sensing signals via the wireless transceiver.

Item A2. The wireless sensor device of Item A1, further comprising: a near-field communication (NFC) transceiver.

Item A3. The wireless sensor device of Item A1 or A2, further comprising: a physiology sensing component that is configured to generate a physiology sensing signal.

Item A4. The wireless sensor device of any one of Item A1-A3, further comprising: a motion sensing component that is configured to generate a motion sensing signal.

Item A5. The wireless sensor device of any one of Item A1-A4, wherein the housing is in a generally rectangular shape.

Item A6. The wireless sensor device of any one of Item A1-A5, wherein the housing has a cross-section area no greater than 45 mm×45 mm.

Item A7. The wireless sensor device of any one of Item A1-A6, wherein the housing is in a generally cylindrical shape.

Item A8. The wireless sensor device of any one of Item A1-A7, further comprising: a battery configured to supply power to the wireless sensor device.

Item A9. The wireless sensor device of any one of Item A1-A8, wherein the wireless transceiver is configured to transmit and receive data in a plurality of radio bands.

Item A10. The wireless sensor device of any one of Item A1-A9, further comprising: a user interface configured to generate an output based on the sensor signal.

Item A11. The wireless sensor device of any one of Item A1-A10, wherein the user interface comprises a touch sensitive device.

Item A12. The wireless sensor device of any one of Item A1-A11, wherein the user interface comprises a display.

Item A13. The wireless sensor device of any one of Item A1-A12, wherein the fastener comprises a snap connector.

Item B1. A wireless sensor device to connect to a supporting physiological sensor having a snap fastener male connector, comprising:
a housing having a snap fastener female connector, the snap fastener female connector configured to mechanically and electrically connect to the snap fastener male connector of the supporting physiological sensor,
a wireless transceiver, and
a plurality of connectors, each connector configured to connect to a sensor,
wherein the wireless sensor device is configured to receive sensing signals from a plurality of sensors via the plurality of connectors and from the supporting physiological sensor and wirelessly transmit a sensor signal indicative to the received sensing signals via the wireless transceiver.

Item B2. The wireless sensor device of Item B1, further comprising: a near-field communication (NFC) transceiver.

Item B3. The wireless sensor device of Item B1 or B2, further comprising: a physiology sensing component that is configured to generate a physiology sensing signal.

Item B4. The wireless sensor device of any one of Item B1-B3, further comprising: a motion sensing component that is configured to generate a motion sensing signal.

Item B5. The wireless sensor device of any one of Item B1-B4, wherein the housing is in a generally rectangular shape.

Item B6. The wireless sensor device of any one of Item B1-B5, wherein the housing has a cross-section area no greater than 45 mm×45 mm.

Item B7. The wireless sensor device of any one of Item B1-B6, wherein the housing is in a generally cylindrical shape.

Item B8. The wireless sensor device of any one of Item B1-B7, further comprising: a battery configured to supply power to the wireless sensor device.

Item B9. The wireless sensor device of any one of Item B1-B8, wherein the wireless transceiver is configured to transmit and receive data in a plurality of radio bands.

Item B10. The wireless sensor device of any one of Item B1-B9, further comprising: a user interface configured to generate an output based on the sensor signal.

Item B11. The wireless sensor device of any one of Item B1-B10, wherein the user interface comprises a touch sensitive device.

Item B12. The wireless sensor device of any one of Item B1-B11, wherein the user interface comprises a display.

Item C1. A wireless physiology monitoring system, comprising:
a plurality of sensors,
a wireless sensor device electrically connected to the plurality of sensors and comprising a first wireless transceiver, the wireless sensor device mechanically and electrically connected to one of the plurality of sensors, the wireless sensor device configured to receive sensing signals from the plurality of sensors and wirelessly transmit a sensor signal indicative to the sensing signals via the first wireless transceiver, and
a wireless adaptor device comprising a second wireless transceiver and configured to wirelessly receive the sensor signal via the second wireless transceiver.

Item C2. The wireless physiology monitoring system of Item C1, further comprising: a physiology monitor connected to the wireless adaptor device.

Item C3. The wireless physiology monitoring system of Item C2, wherein the physiology monitor is connected to the wireless adaptor device via a cable.

Item C4. The wireless physiology monitoring system of any one of Item C1-C3, wherein the wireless sensor device further comprises a first NFC transceiver.

Item C5. The wireless physiology monitoring system of Item C4, wherein the wireless adaptor device further comprises a second NFC transceiver, and wherein the wireless sensor device is configured communicate to the wireless adaptor device via NFC.

Item C6. The wireless physiology monitoring system of Item C5, wherein the wireless sensor device is configured to communicate wireless identification to the wireless adaptor device via NFC.

Item C7. The wireless physiology monitoring system of Item C6, wherein the wireless sensor device is configured to establish wireless communication with the wireless adaptor device using the wireless identification.

Item C8. The wireless physiology monitoring system of Item C5, wherein the wireless sensor device is configured to communicate wireless encryption information to the wireless adaptor device via NFC.

Item C9. The wireless physiology monitoring system of Item C8, wherein the wireless sensor device is configured to establish a secured wireless communication with the wireless adaptor device using the wireless identification and the wireless encryption information.

Item C10. The wireless physiology monitoring system of any one of Item C1-C9, wherein the wireless sensor device further comprises a physiology sensing component that is configured to generate a physiology sensing signal.

Item C11. The wireless physiology monitoring system of any one of Item C1-C10, wherein the wireless sensor device further comprises a motion sensing component that is configured to generate a motion sensing signal.

Item C12. The wireless physiology monitoring system of any one of Item C1-C11, wherein the wireless sensor device further comprises a housing having a fastener to mechanically and electrically connected to the one of the plurality of sensors.

Item C13. The wireless physiology monitoring system of Item C12, wherein the fastener is a snap fastener female connector.

Item C14. The wireless physiology monitoring system of Item C12, wherein the housing is in a generally rectangular shape.

Item C15. The wireless physiology monitoring system of Item C14, wherein the housing has a size no greater than 45×45×20 mm.

Item C16. The wireless physiology monitoring system of Item C12, wherein the housing is in a generally cylindrical shape.

Item C17. The wireless physiology monitoring system of any one of Item C1-C16, wherein the wireless sensor device further comprises a battery configured to supply power to the wireless sensor device.

Item C18. The wireless physiology monitoring system of any one of Item C1-C17, wherein the first wireless transceiver is configured to transmit and receive data in a plurality of radio bands.

Item C19. The wireless physiology monitoring system of any one of Item C1-C18, wherein the wireless sensor device further comprises a first user interface configured to generate an output based on the sensor signal.

Item C20. The wireless physiology monitoring system of any one of Item C1-C19, wherein the second wireless transceiver is configured to transmit and receive data in a plurality of radio bands.

Item C21. The wireless physiology monitoring system of any one of Item C1-C20, wherein the wireless adaptor device comprises a docking component and a wireless component, and wherein the wireless component comprises the second wireless transceiver.

Item C22. The wireless physiology monitoring system of Item C21, wherein the docking component is configured to connect to a physiology monitor.

Item C23. The wireless physiology monitoring system of Item C1, wherein the wireless adaptor device further comprises a second user interface and configured to generate an output based on the received sensor signal.

Item C24. The wireless physiology monitoring system of Item C23, wherein the second user interface comprises a display.

Item C25. The wireless physiology monitoring system of Item C23, wherein the second user interface comprises a touch sensitive device.

Item C26. The wireless physiology monitoring system of any one of Item C1-C25, wherein the plurality of sensors comprises at least one of ECG electrodes, $SpO_2$ sensors, body temperature sensors, blood pressure sensors, and acoustical sensors.

Item D1. A method of monitoring a physiological condition with a plurality of sensors, comprising:
placing a wireless adaptor device proximate to a wireless sensor device, the wireless sensor device electrically connected to the plurality of sensors and having a first wireless transceiver and a first NFC transceiver, the wireless adaptor device having a second wireless transceiver and a second NFC transceiver;
transmitting, by the wireless adaptor device, wireless identification of the wireless adaptor device to the wireless sensor device via a NFC communication;
establishing, by the wireless sensor device, a wireless communication with the wireless adaptor device using the wireless identification of the wireless adaptor device;
collecting, by the wireless sensor device, sensing signals generated by the plurality of sensors,
generating, by the wireless sensor device, a sensor signal indicative to the sensing signals;
transmitting, by the wireless sensor device, the sensor signal via the established wireless communication; and
receiving, by the wireless adaptor device, the sensor signal via the established wireless communication.

Item D2. The method of Item D1, further comprising: transmitting, via the wireless adaptor device, wireless encryption information of the wireless adaptor device to the wireless sensor device via the NFC communication, and wherein the established wireless communication is a secured wireless communication using the wireless encryption information of the wireless adaptor device.

Item D3. The method of Item D1 or D2, further comprising: activating, by the wireless adaptor device, the wireless sensor device using NFC interrogation.

Item D4. The method of any one of Item D1-D3, further comprising: supplying power to the wireless sensor device using NFC interrogation.

Item D5. The method of any one of Item D1-D4, further comprising: transmitting, by the wireless adaptor device, a signal indicative to the sensor signal to a physiology monitor.

Item D6. The method of Item D5, wherein the physiology monitor is connected to the wireless adaptor device via a cable.

Item D7. The method of any one of Item D1-D6, wherein the wireless sensor device further comprises a physiology sensing component that is configured to generate a physiology sensing signal, and wherein the sensor signal comprises an indication to the physiology sensing signal.

Item D8. The method of any one of Item D1-D7, wherein the wireless sensor device further comprises a motion sensing component that is configured to generate a motion sensing signal and wherein the sensor signal comprises an indication to the motion sensing signal.

Item D9. The method of any one of Item D1-D8, further comprising: attaching the wireless sensor device to one of the plurality of sensors by a fastener on a housing of the wireless sensor device, wherein the wireless sensor is mechanically and electrically connected to the one of the plurality of sensors.

Item D10. The method of Item D9, wherein the fastener is a snap fastener female connector.

Item D11. The method of Item D9, wherein the housing of the wireless sensor device is in a generally rectangular shape.

Item D12. The method of Item D11, wherein the housing of the wireless sensor device has a cross-section area no greater than 45 mm×45 mm.

Item D13. The method of Item D9, wherein the housing is in a generally cylindrical shape.

Item D14. The method of any one of Item D1-D13, wherein the wireless sensor device further comprises a battery configured to supply power to the wireless sensor device.

Item D15. The method of any one of Item D1-D14, wherein the first wireless transceiver is configured to transmit and receive data in a plurality of radio bands.

Item D16. The method of any one of Item D1-D15, further comprising: generating, by the wireless sensor device, an output based on the sensor signal on a first user interface of the wireless sensor device.

Item D17. The method of any one of Item D1-D16, wherein the second wireless transceiver is configured to transmit and receive data in a plurality of radio bands.

Item D18. The method of any one of Item D1-D17, wherein the wireless adaptor device comprises a docking component and a wireless component, and wherein the wireless component comprises the second wireless transceiver.

Item D19. The method of Item D18, wherein the docking component is configured to connect to a physiology monitor.

Item D20. The method of any one of Item D1-D19, wherein the wireless adaptor device further comprises a second user interface and configured to generate an output based on the received sensor signal.

Item D21. The method of Item D20, wherein the second user interface comprises a display.

Item D22. The method of Item D20, wherein the second user interface comprises a touch sensitive device.

Item D23. The method of Item D16, wherein the second user interface comprises a display.

Item D24. The method of Item D16, wherein the second user interface comprises a touch sensitive device.

Item E1. A method of monitoring a physiological condition with a plurality of sensors, comprising:

placing a wireless adaptor device proximate to a wireless sensor device, the wireless sensor device electrically connected to the plurality of sensors and having a first wireless transceiver and a first NFC transceiver, the wireless adaptor device having a second wireless transceiver and a second NFC transceiver;

transmitting, by the wireless sensor device, wireless identification of the wireless sensor device to the wireless adaptor device via a NFC communication;

establishing, by the wireless adaptor device, a wireless communication with the wireless sensor device using the wireless identification of the wireless sensor device;

collecting, by the wireless sensor device, sensing signals generated by the plurality of sensors;

generating, by the wireless sensor device, a sensor signal indicative to the sensing signals;

transmitting, by the wireless sensor device, the sensor signal via the established wireless communication; and receiving, by the wireless adaptor device, the sensor signal via the established wireless communication.

Item E2. The method of Item E1, further comprising:

transmitting, via the wireless sensor device, wireless encryption information of the wireless sensor device to the wireless adaptor device via the NFC communication, and wherein the established wireless communication is a secured wireless communication using the wireless encryption information of the wireless sensor device.

Item E3. The method of Item E1 or E2, further comprising: activating, by the wireless adaptor device, the wireless sensor device using NFC interrogation.

Item E4. The method of any one of Item E1-E3, further comprising: supplying power to the wireless sensor device using NFC interrogation.

Item E5. The method of any one of Item E1-E4, further comprising: transmitting, by the wireless adaptor device, a signal indicative to the sensor signal to a physiology monitor.

Item E6. The method of Item E5, wherein the physiology monitor is connected to the wireless adaptor device via a cable.

Item E7. The method of any one of Item E1-E6, wherein the wireless sensor device further comprises a physiology sensing component that is configured to generate a physiology sensing signal, and wherein the sensor signal comprises an indication to the physiology sensing signal.

Item E8. The method of any one of Item E1-E7, wherein the wireless sensor device further comprises a motion sensing component that is configured to generate a motion sensing signal and wherein the sensor signal comprises an indication to the motion sensing signal.

Item E9. The method of any one of Item E1-E8, further comprising: attaching the wireless sensor device to one of the plurality of sensors by a fastener on a housing of the wireless sensor device, wherein the wireless sensor is mechanically and electrically connected to the one of the plurality of sensors.

Item E10. The method of Item E9, wherein the fastener is a snap fastener female connector.

Item E11. The method of Item E9, wherein the housing of the wireless sensor device is in a generally rectangular shape.

Item E12. The method of Item E11, wherein the housing of the wireless sensor device has a cross-section area no greater than 45 mm×45 mm.

Item E13. The method of Item E9, wherein the housing is in a generally cylindrical shape.

Item E14. The method of any one of Item E1-E13, wherein the wireless sensor device further comprises a battery configured to supply power to the wireless sensor device.

Item E15. The method of any one of Item E1-E14, wherein the first wireless transceiver is configured to transmit and receive data in a plurality of radio bands.

Item E16. The method of any one of Item E1-E15, further comprising: generating, by the wireless sensor device, an output based on the sensor signal on a first user interface of the wireless sensor device.

Item E17. The method of any one of Item E1-E16, wherein the second wireless transceiver is configured to transmit and receive data in a plurality of radio bands.

Item E18. The method of any one of Item E1-E17, wherein the wireless adaptor device comprises a docking component and a wireless component, and wherein the wireless component comprises the second wireless transceiver.

Item E19. The method of Item E18, wherein the docking component is configured to connect to a physiology monitor.

Item E20. The method of any one of Item E1-E19, wherein the wireless adaptor device further comprises a second user interface and configured to generate an output based on the received sensor signal.

Item E21. The method of Item E20, wherein the second user interface comprises a display.

Item E22. The method of Item E20, wherein the second user interface comprises a touch sensitive device.

Item E23. The method of Item E16, wherein the second user interface comprises a display.

Item E24. The method of Item E16, wherein the second user interface comprises a touch sensitive device.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices falling within the spirit and scope of the invention as defined by the appended claims and their equivalents.

What is claimed is:

1. A method of monitoring a physiological condition using a plurality of sensors, the method comprising:
   positioning a wireless adaptor device at a first distance from a wireless sensor device, the wireless sensor device being mechanically and electrically connected to at least one respective sensor of the plurality of sensors;
   establishing, via near field communication (NFC), by a first NFC transceiver of the wireless sensor device, a pairing with a wireless adaptor device via a second NFC transceiver of a second wireless transceiver of the wireless adaptor device;
   transmitting, by the first NFC transceiver of the wireless sensor device, via the NFC, wireless identification information to the wireless adaptor device;
   establishing, by the wireless sensor device, a wireless communication session with the wireless adaptor device using the wireless identification information, the wireless communication session being different from the pairing established via the NFC;
   repositioning the wireless adaptor device at a second distance from the wireless sensor device, the second distance being greater than the first distance;
   collecting, by the wireless sensor device, sensing signals generated by the plurality of sensors;
   generating, by the wireless sensor device, a sensor signal indicative of the sensing signals; and
   transmitting, by the wireless sensor device, to the wireless adaptor device the sensor signal over the established wireless communication session.

2. The method of claim 1, further comprising transmitting, by the wireless sensor device, wireless encryption information to the wireless adaptor device via the established wireless communication session, wherein the established wireless communication session is a secured wireless communication session established using the wireless encryption information.

3. The method of claim 1, further comprising activating, by the wireless adaptor device, the wireless sensor device using NFC interrogation while the wireless adaptor device is positioned at the first distance from the wireless sensor device.

4. A method of monitoring a physiological condition using a plurality of sensors, the method comprising:
   positioning a wireless adaptor device at a first distance from a wireless sensor device, the wireless sensor device being mechanically and electrically connected to at least one respective sensor of the plurality of sensors, wherein the wireless sensor device comprises a first wireless transceiver and a first near field communication (NFC) transceiver, and wherein the wireless adaptor device comprises a second wireless transceiver and a second NFC transceiver,
   wirelessly transmitting, by the wireless sensor device, wireless identification of the wireless sensor device to the wireless adaptor device via NFC using the first NFC transceiver;
   establishing, by the wireless adaptor device, a wireless communication session with the wireless sensor device by pairing the wireless sensor device and the wireless adaptor device using the wireless identification of the wireless sensor device, the wireless communication session conforming to an 802.11 communication protocol;
   repositioning the wireless adaptor device at a second distance from the wireless sensor device, the second distance being greater than the first distance;
   collecting, by the wireless sensor device, sensing signals generated by the plurality of sensors, the sensing signals are distinct from communications exchanged over the wireless communication session;
   generating, by the wireless sensor device, a sensor signal indicative of the sensing signals; and
   transmitting, by the wireless sensor device, the sensor signal via the established wireless communication session.

5. The method of claim 4, further comprising transmitting, by the wireless sensor device, wireless encryption information of the wireless sensor device to the wireless adaptor device via the wireless communication session, wherein the established wireless communication session is a secured wireless communication session established using the wireless encryption information of the wireless sensor device.

6. The method of claim 4, further comprising activating, by the wireless adaptor device, the wireless sensor device at least in part by:
   interrogating, by the wireless adaptor device, the wireless sensor device via an electromagnetic field associated with an NFC pairing of the first NFC transceiver and the second NFC transceiver; and
   supplying, by the wireless adaptor device, power to the wireless sensor device while the NFC pairing is active.

7. The method of claim 1, wherein the wireless communication session conforms to an 802.11 communication protocol.

8. The method of claim 1, wherein the first distance is within an NFC range, and wherein the second distance is greater than an NFC range.

9. The method of claim 1, wherein the plurality of sensors include one or more of electrocardiography (ECG) electrodes, oxygen saturation sensors, body temperature sensors, blood pressure sensors, or acoustical sensors.

10. The method of claim 4, wherein the first distance is within an NFC range, and wherein the second distance is greater than an NFC range and within an 802.11 communication range.

11. The method of claim 4, wherein the plurality of sensors include one or more of electrocardiography (ECG) electrodes, oxygen saturation sensors, body temperature sensors, blood pressure sensors, or acoustical sensors.

* * * * *